(12) United States Patent
Mazanec et al.

(10) Patent No.: US 12,081,061 B2
(45) Date of Patent: Sep. 3, 2024

(54) PREDICTING A CUMULATIVE THERMAL DOSE IN IMPLANTABLE BATTERY RECHARGE SYSTEMS AND METHODS

(71) Applicant: Envoy Medical Corporation, White Bear Lake, MN (US)

(72) Inventors: Paul R. Mazanec, Ham Lake, MN (US); Joshua J. Wibben, New Brighton, MN (US); Benjamin R. Whittington, Maplewood, MN (US)

(73) Assignee: Envoy Medical Corporation, White Bear Lake, MN (US)

( * ) Notice: Subject to any disclaimer, the term of this patent is extended or adjusted under 35 U.S.C. 154(b) by 714 days.

(21) Appl. No.: 17/182,470

(22) Filed: Feb. 23, 2021

(65) Prior Publication Data

US 2022/0266016 A1    Aug. 25, 2022

(51) Int. Cl.
*H02J 7/00* (2006.01)
*A61N 1/05* (2006.01)
(Continued)

(52) U.S. Cl.
CPC ...... *H02J 7/007192* (2020.01); *A61N 1/0541* (2013.01); *A61N 1/36038* (2017.08);
(Continued)

(58) Field of Classification Search
CPC .............. A61N 1/36038; A61N 1/0541; A61N 1/3787; G01K 1/024; H02J 7/00032;
(Continued)

(56) References Cited

U.S. PATENT DOCUMENTS 2,827,041 A    3/1958 Pierson
4,400,590 A    8/1983 Michelson
(Continued)

FOREIGN PATENT DOCUMENTS

CN    104394930 A    3/2015
CN    110086237 A    8/2019
(Continued)

OTHER PUBLICATIONS

Mazanec et al., unpublished U.S. Appl. No. 17/006,467, entitled Programming of Cochlear Implant Accessories, filed Aug. 28, 2020, 74 pages.
(Continued)

*Primary Examiner* — Richard Isla
*Assistant Examiner* — Manuel Hernandez
(74) *Attorney, Agent, or Firm* — Fredrikson & Byron, P.A.

(57) ABSTRACT

Systems including a rechargeable energy storage device can include a temperature sensor and a controller configured to receive temperature information representative of a temperature proximate the rechargeable energy storage device. The controller can be configured to receive or determine a second charging parameter associated with the charging of the rechargeable energy storage device, such as charging duration, and compare the temperature or the second parameter to a corresponding threshold. If the parameter associated with the charging the rechargeable energy storage device (e.g., charging duration and/or the temperature information) exceeds the corresponding threshold, the controller can reduce the amount of electrical current provided to the rechargeable energy storage device during charging. This can enable charging the rechargeable energy storage device at a maximum rate without exceeding thermal dose safety standards associated with charging the rechargeable energy storage device.

26 Claims, 9 Drawing Sheets

(51) Int. Cl.
  *A61N 1/36* (2006.01)
  *A61N 1/378* (2006.01)
  *G01K 1/024* (2021.01)
  *H02J 50/10* (2016.01)

(52) U.S. Cl.
  CPC .......... *A61N 1/3787* (2013.01); *G01K 1/024* (2013.01); *H02J 7/00032* (2020.01); *H02J 7/0048* (2020.01); *H02J 7/0071* (2020.01); *H02J 50/10* (2016.02)

(58) Field of Classification Search
  CPC .. H02J 7/0048; H02J 7/0071; H02J 7/007192; H02J 50/10
  USPC .................................................. 320/108, 150
  See application file for complete search history.

(56) References Cited

U.S. PATENT DOCUMENTS

| | | | |
|---|---|---|---|
| 4,495,384 | A | 1/1985 | Scott et al. |
| 4,729,366 | A | 3/1988 | Schaefer |
| 4,850,962 | A | 7/1989 | Schaefer |
| 4,918,745 | A | 4/1990 | Hutchison |
| 5,540,095 | A | 7/1996 | Sherman et al. |
| 5,762,583 | A | 6/1998 | Adams et al. |
| 6,195,585 | B1 | 2/2001 | Karunasiri et al. |
| 6,212,431 | B1 | 4/2001 | Hahn et al. |
| 6,259,951 | B1 | 7/2001 | Kuzma et al. |
| 6,272,382 | B1 | 8/2001 | Faltys et al. |
| 6,308,101 | B1 | 10/2001 | Faltys et al. |
| 6,358,281 | B1 | 3/2002 | Berrang et al. |
| 7,225,028 | B2 | 5/2007 | Della Santina et al. |
| 7,319,906 | B2 | 1/2008 | Kuzma et al. |
| 7,376,563 | B2 | 5/2008 | Leysieffer et al. |
| 7,524,278 | B2 | 4/2009 | Madsen et al. |
| 8,148,950 | B2* | 4/2012 | Matsuura .......... H02J 7/007194 320/132 |
| 8,554,329 | B1 | 10/2013 | Mann et al. |
| 8,655,449 | B2 | 2/2014 | Haller et al. |
| 9,126,488 | B2* | 9/2015 | Hiroe .......................... H02J 7/04 |
| 9,205,272 | B2 | 12/2015 | Suaning et al. |
| 9,504,076 | B2 | 11/2016 | El-Hoiydi et al. |
| 9,539,430 | B2 | 1/2017 | Mishra et al. |
| 9,716,952 | B2 | 7/2017 | Mauger |
| 10,862,328 | B2 | 12/2020 | Cong et al. |
| 11,515,587 | B2* | 11/2022 | Stewart ............. H02J 7/007194 |
| 2002/0039425 | A1 | 4/2002 | Burnett et al. |
| 2002/0099421 | A1 | 7/2002 | Goldsmith et al. |
| 2004/0230254 | A1 | 11/2004 | Harrison et al. |
| 2005/0033384 | A1 | 2/2005 | Sacha |
| 2005/0197677 | A1 | 9/2005 | Stevenson |
| 2006/0122664 | A1 | 6/2006 | Sacha et al. |
| 2006/0183965 | A1 | 8/2006 | Kasic, II et al. |
| 2008/0195179 | A1 | 8/2008 | Quick |
| 2008/0300658 | A1 | 12/2008 | Meskens |
| 2009/0018616 | A1 | 1/2009 | Quick et al. |
| 2009/0082831 | A1 | 3/2009 | Paul et al. |
| 2009/0187233 | A1 | 7/2009 | Stracener |
| 2009/0192565 | A1 | 7/2009 | Lee et al. |
| 2010/0010582 | A1* | 1/2010 | Carbunaru ................ G01J 5/07 320/108 |
| 2010/0019729 | A1* | 1/2010 | Kaita .................... H02J 7/1423 320/134 |
| 2010/0030012 | A1 | 2/2010 | Meskens |
| 2010/0042183 | A1 | 2/2010 | Beck |
| 2010/0317913 | A1 | 12/2010 | Conn et al. |
| 2011/0082521 | A1 | 4/2011 | Botros et al. |
| 2011/0116669 | A1 | 5/2011 | Karunasiri |
| 2011/0137180 | A1 | 6/2011 | Johnson et al. |
| 2011/0144719 | A1 | 6/2011 | Perkins et al. |
| 2011/0160808 | A1 | 6/2011 | Lyden et al. |
| 2011/0280426 | A1 | 11/2011 | Bachler |
| 2011/0295331 | A1 | 12/2011 | Wells et al. |
| 2012/0063610 | A1 | 3/2012 | Kaulberg et al. |
| 2012/0215285 | A1 | 8/2012 | Tahmasian et al. |
| 2012/0277835 | A1 | 11/2012 | Della Santina et al. |
| 2013/0018216 | A1 | 1/2013 | Beckerle et al. |
| 2013/0023953 | A1 | 1/2013 | van den Honert |
| 2013/0193914 | A1 | 8/2013 | Gaddam et al. |
| 2013/0197613 | A1* | 8/2013 | Kelly .................. A61N 1/3787 607/96 |
| 2013/0223664 | A1 | 8/2013 | Meskens et al. |
| 2013/0238055 | A1 | 9/2013 | Marnfeldt et al. |
| 2013/0268025 | A1 | 10/2013 | Ranu |
| 2013/0278226 | A1 | 10/2013 | Cong et al. |
| 2013/0317584 | A1 | 11/2013 | Stevenson et al. |
| 2014/0058482 | A1 | 2/2014 | Gupta et al. |
| 2014/0070761 | A1* | 3/2014 | Labbe .................... A61N 1/378 320/108 |
| 2014/0155947 | A1 | 6/2014 | Kroll et al. |
| 2014/0247954 | A1 | 9/2014 | Hall et al. |
| 2014/0270211 | A1 | 9/2014 | Solum et al. |
| 2014/0275730 | A1 | 9/2014 | Lievens et al. |
| 2014/0309712 | A1 | 10/2014 | Masaki et al. |
| 2014/0350652 | A1 | 11/2014 | Suwito |
| 2015/0125012 | A1 | 5/2015 | Sabin |
| 2015/0174416 | A1 | 6/2015 | Angara et al. |
| 2015/0224312 | A1 | 8/2015 | Platz et al. |
| 2015/0256945 | A1 | 9/2015 | Mazanec |
| 2015/0374988 | A1 | 12/2015 | Laudanski |
| 2015/0375003 | A1 | 12/2015 | Meskens |
| 2016/0050500 | A1 | 2/2016 | Liao et al. |
| 2016/0227333 | A1 | 8/2016 | Babico |
| 2017/0043162 | A1 | 2/2017 | Lopez-Poveda |
| 2017/0077938 | A1 | 3/2017 | Heubi |
| 2017/0094396 | A1 | 3/2017 | Chandramohan et al. |
| 2017/0161449 | A1 | 6/2017 | Meskens |
| 2017/0259072 | A1 | 9/2017 | Newham et al. |
| 2017/0360364 | A1 | 12/2017 | Heasman et al. |
| 2018/0028811 | A1 | 2/2018 | Van Gerwen et al. |
| 2018/0028827 | A1 | 2/2018 | Schilling et al. |
| 2018/0041848 | A1 | 2/2018 | Nielsen et al. |
| 2018/0050197 | A1 | 2/2018 | Mazanec et al. |
| 2018/0050198 | A1 | 2/2018 | Mazanec et al. |
| 2018/0050203 | A1 | 2/2018 | Mazanec et al. |
| 2018/0059870 | A1 | 3/2018 | Krah |
| 2018/0069272 | A1* | 3/2018 | Seo ........................ B60L 3/0046 |
| 2018/0264269 | A1 | 9/2018 | Meadows |
| 2018/0317027 | A1 | 11/2018 | Bolner et al. |
| 2018/0333577 | A1 | 11/2018 | Nygard et al. |
| 2018/0361151 | A1 | 12/2018 | Ridler et al. |
| 2019/0045308 | A1 | 2/2019 | Chen et al. |
| 2019/0046116 | A1 | 2/2019 | Shah et al. |
| 2019/0190296 | A1* | 6/2019 | Paralikar .............. A61N 1/3787 |
| 2019/0344073 | A1 | 11/2019 | Baker et al. |
| 2020/0054877 | A1 | 2/2020 | Calixto et al. |
| 2020/0238075 | A1 | 7/2020 | Mazanec et al. |
| 2020/0269034 | A1 | 8/2020 | Mazanec et al. |
| 2020/0269035 | A1 | 8/2020 | Mazanec et al. |
| 2020/0269047 | A1 | 8/2020 | Mazanec et al. |
| 2020/0269048 | A1 | 8/2020 | Mazanec et al. |
| 2020/0269057 | A1 | 8/2020 | Mazanec et al. |
| 2020/0269058 | A1 | 8/2020 | Mazanec et al. |
| 2020/0366118 | A1* | 11/2020 | Lee ................... H02J 7/007192 |
| 2021/0053457 | A1* | 2/2021 | Jeon .................. H02J 7/007192 |
| 2021/0084417 | A1 | 3/2021 | Bagazov et al. |
| 2021/0121707 | A1* | 4/2021 | Fried .................... A61N 1/3787 |
| 2021/0135704 | A1 | 5/2021 | El-Hoiydi et al. |
| 2021/0187293 | A1 | 6/2021 | Friedling |
| 2021/0361194 | A1 | 11/2021 | Arab et al. |
| 2022/0203104 | A1* | 6/2022 | Hernandez ........... A61N 1/3787 |
| 2022/0339445 | A1 | 10/2022 | Litvak et al. |

FOREIGN PATENT DOCUMENTS

| | | |
|---|---|---|
| DE | 4419070 A1 | 12/1994 |
| DE | 60107062 T2 | 11/2005 |
| DE | 102013214049 B4 | 3/2015 |
| EP | 1043914 A2 | 10/2000 |
| EP | 1683544 B1 | 11/2010 |
| EP | 2884766 B1 | 2/2018 |
| EP | 3120579 B1 | 2/2020 |
| TW | 201142830 A | 12/2011 |

(56) References Cited

FOREIGN PATENT DOCUMENTS

| WO | 2007137032 A2 | 11/2007 |
| WO | 2010056768 A1 | 5/2010 |
| WO | 2014037888 A1 | 3/2014 |
| WO | 2015077773 A1 | 5/2015 |
| WO | 2016122606 A1 | 8/2016 |
| WO | 2017100866 A1 | 6/2017 |
| WO | 2018035329 A1 | 2/2018 |
| WO | 2018144732 A1 | 8/2018 |
| WO | 2020172500 A1 | 8/2020 |

OTHER PUBLICATIONS

Mazanec et al., unpublished U.S. Appl. No. 17/109,303, entitled Implantable Cochlear System With Inner Ear Sensor, filed Dec. 2, 2020, 54 pages.

Mazanec et al., unpublished U.S. Appl. No. 17/109,304, entitled Combination Hearing Aid and Cochlear Implant System, filed Dec. 2, 2020, 55 pages.

Mazanec et al., unpublished U.S. Appl. No. 17/109,305, entitled Cochlear Implant Stimulation Calibration, filed Dec. 2, 2020, 53 pages.

PCT International Search Report and Written Opinion dated May 23, 2022 for related Intl. App. No. PCT/US2022/017136, 12 pgs.

\* cited by examiner

PREDICTING A CUMULATIVE THERMAL DOSE IN IMPLANTABLE BATTERY RECHARGE SYSTEMS AND METHODS

BACKGROUND

A cochlear implant is an electronic device that may be at least partially implanted surgically into the cochlea, the hearing organ of the inner ear, to provide improved hearing to a patient. Cochlear implants may include implantable components that may require an electrical current and/or power to operate, such as power from an implantable battery.

In some cases, the implantable battery may be charged by an external power source. However in some embodiments, the charging of the battery may lead to the heating of the implantable battery, surrounding tissue, and/or surrounding components. If the temperature gets too high and/or sustains a high temperature for too long, the cochlear implant may damage the wearer's surrounding tissue and/or fail medical safety standards.

SUMMARY

Some aspects of the disclosure are generally directed toward cochlear implant systems and methods for charging an implantable rechargeable energy storage device, such as a battery or other energy storage device for providing electrical power to an implanted medical device. In some examples, the system may comprise an implantable battery and/or communication module as well as a controller. The implantable battery and/or communication module may be configured to provide electrical power to one or more implanted system components. Exemplary implantable battery and/or communication modules may comprise a rechargeable energy storage device, a temperature sensor, and a first wireless charging interface. The controller may be configured to receive temperature information representative of a temperature in the implantable battery and/or communication module at a first time as well as receive or determine a second charging parameter associated with the charging of the rechargeable energy storage device. In some embodiments, the controller may be further configured to compare a parameter associated with charging the rechargeable energy storage device to a corresponding threshold and if the parameter associated with the charging the rechargeable energy storage device exceeds the corresponding threshold, reduce the amount of electrical current provided to the rechargeable energy storage device during charging.

In some embodiments, the second charging parameter may comprise an amount of time the rechargeable energy storage device has been charging. In such embodiments, comparing the parameter associated with the charging of the rechargeable energy storage device to a corresponding threshold may comprise comparing the amount of time the rechargeable energy storage device has been charging to a duration threshold and stopping charging the rechargeable energy storage device if the amount of time the rechargeable energy storage device has been charging exceeds the duration threshold.

Additionally or alternatively, the second charging parameter may comprise an amount of current being provided to the rechargeable energy storage device. In such embodiments, the controller may be configured to receive or determine an amount of current being provided to the rechargeable energy storage device during charging as well as receive state-of-charge information representative of a charge of the rechargeable energy storage device. The controller may be further configured to predict an amount of time remaining until the rechargeable energy storage device is fully charged based on the received state-of-charge information and determined amount of current and predict a cumulative thermal dose associated with charging the rechargeable energy storage device to a fully charged state based on the received temperature information and the predicted amount of time remaining until the rechargeable energy storage device is fully charged.

DETAILED DESCRIPTION

Figure 1:
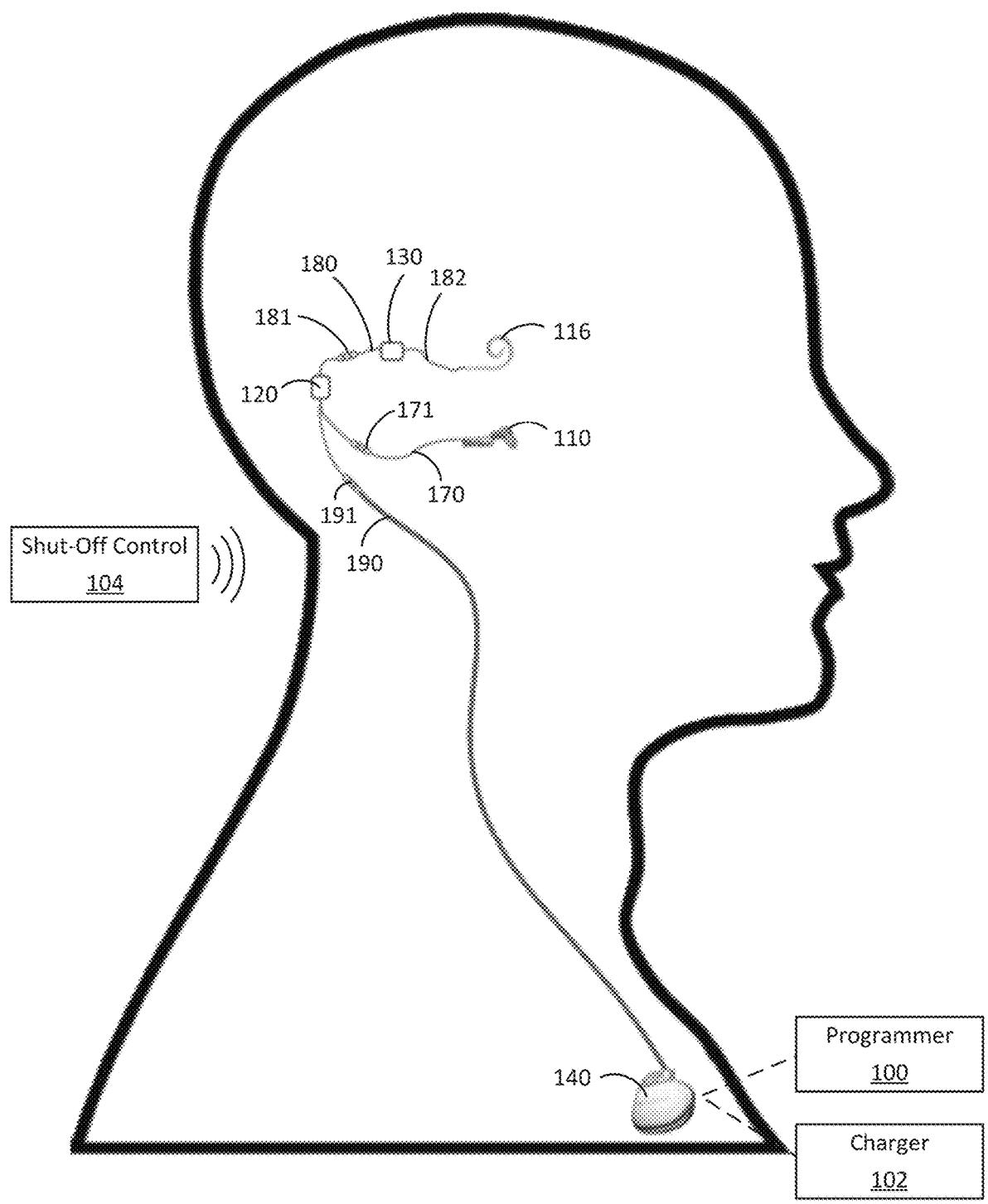
FIG. 1 shows a schematic illustration of a fully implantable cochlear implant system.

FIG. 1 shows a schematic illustration of a fully implantable cochlear implant system. The system of FIG. 1 includes a middle ear sensor 110 in communication with a signal processor 120. The middle ear sensor 110 can be configured to detect incoming sound waves, for example, using the ear structure of a patient. The signal processor 120 can be configured to receive a signal from the middle ear sensor 110 and produce an output signal based thereon. For example, the signal processor 120 can be programmed with instructions to output a certain signal based on a received signal. In some embodiments, the output of the signal processor 120 can be calculated using an equation based on received input signals. Alternatively, in some embodiments, the output of the signal processor 120 can be based on a lookup table or other programmed (e.g., in memory) correspondence between the input signal from the middle ear sensor 110 and the output signal. While not necessarily based explicitly on a function, the relationship between the input to the signal processor 120 (e.g., from the middle ear sensor 110) and the output of the signal processor 120 is referred to as the transfer function of the signal processor 120.

In various examples, the signal processor 120 can comprise any variety of components, for example, digital and/or analog processing components. In some embodiments, signal processor 120 comprises a digital signal processor, one or more microprocessors, microcontrollers, application specific integrated circuits (ASICs) or the like. Supporting circuitry for one or more such components can also be included as a part of the signal processor. In some embodiments, the signal processor can include or otherwise communicate with a memory containing programming for operating one or more components. Additionally or alternatively, in some embodiments, the signal processor can include one or more additional components. For example, in some embodiments, signal processor can include an embedded microphone or other sensor configured to detect incoming sound waves.

The system of FIG. 1 further includes a cochlear electrode 116 implanted into the cochlear tissues of a patient. The cochlear electrode 116 is in electrical communication with an electrical stimulator 130, which can be configured to provide electrical signals to the cochlear electrode 116 in response to input signals received by the electrical stimulator 130. In some examples, the cochlear electrode 116 is fixedly attached to the electrical stimulator 130. In other examples, the cochlear electrode 116 is removably attached to the electrical stimulator 130. As shown, the electrical stimulator 130 is in communication with the signal processor 120. In some embodiments, the electrical stimulator 130 provides electrical signals to the cochlear electrode 116 based on output signals from the signal processor 120.

In various embodiments, the cochlear electrode 116 can include any number of contact electrodes in electrical contact with different parts of the cochlear tissue. In such embodiments, the electrical stimulator 130 can be configured to provide electrical signals to any number of such contact electrodes to stimulate the cochlear tissue. For example, in some embodiments, the electrical stimulator 130 is configured to activate different contact electrodes or combinations of contact electrodes of the cochlear electrode 116 in response to different input signals received from the signal processor 120. This can help the patient differentiate between different input signals.

During exemplary operation, the middle ear sensor 110 detects audio signals, for example, using features of the patient's ear anatomy as described elsewhere herein and in U.S. Patent Publication No. 2013/0018216, which is hereby incorporated by reference in its entirety. The signal processor 120 can receive such signals from the middle ear sensor 110 and produce an output to the electrical stimulator 130 based on the transfer function of the signal processor 120. The electrical stimulator 130 can then stimulate one or more contact electrodes of the cochlear electrode 116 based on the received signals from the signal processor 120.

Figure 2:
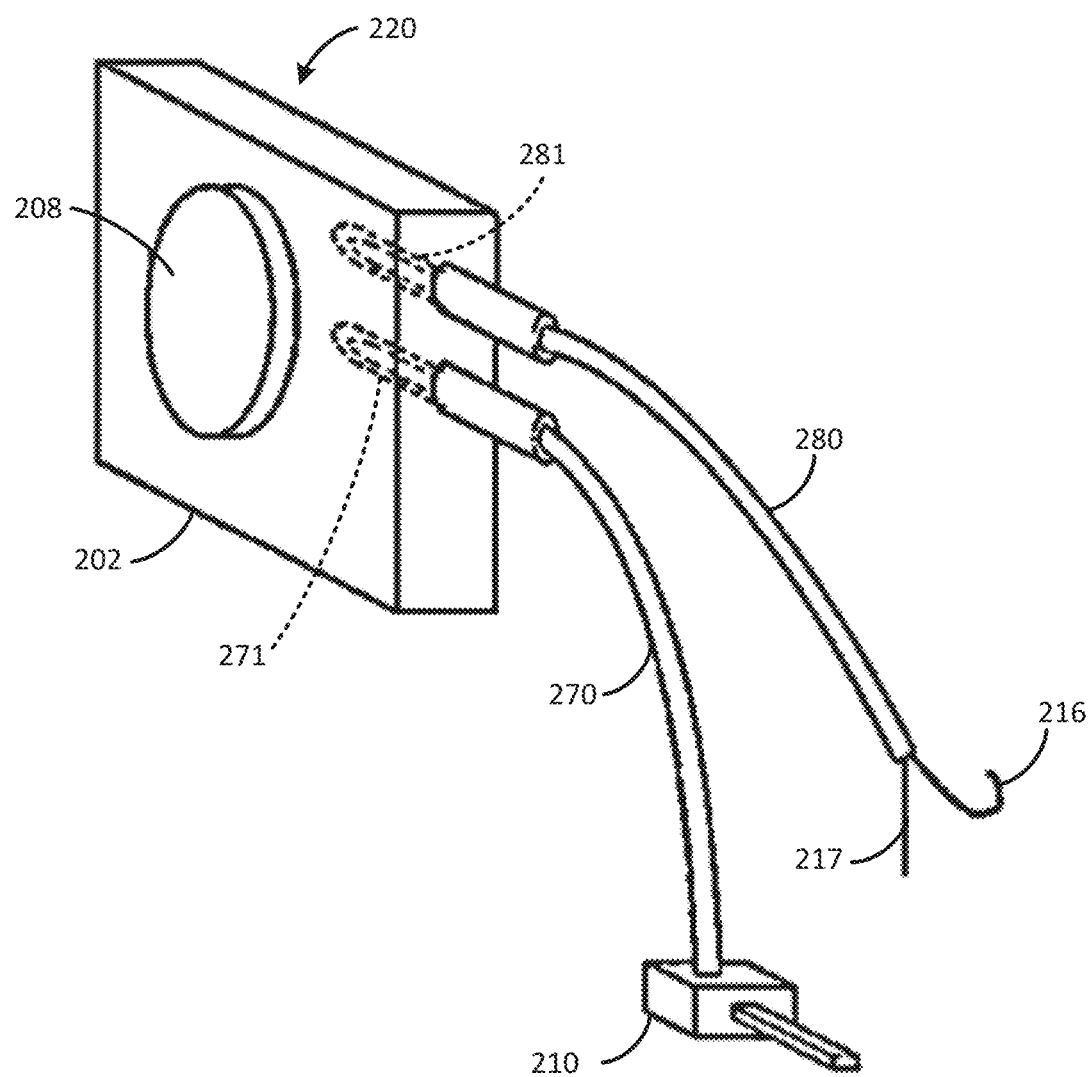
FIG. 2 shows an embodiment of a fully-implantable cochlear implant.

Referring to FIG. 2, an embodiment of a fully-implantable cochlear implant is shown. The device in this embodiment includes a processor 220 (e.g., signal processor), a sensor 210, a first lead 270 connecting the sensor 210 to the processor 220, and a combination lead 280 attached to the processor 220, wherein combination lead 280 contains both a ground electrode 217 and a cochlear electrode 216. The illustrated processor 220 includes a housing 202, a coil 208, first female receptacle 271 and second female receptacle 281 for insertion of the leads 270 and 280, respectively.

In some embodiments, coil 208 can receive power and/or data from an external device, for instance, including a transmission coil (not shown). Some such examples are described in U.S. Patent Publication No. 2013/0018216, which is incorporated by reference. In other examples, processor 220 is configured to receive power and/or data from other sources, such as an implantable battery and/or communication module as shown in FIG. 1. An implantable battery and/or communication module can include a rechargeable energy storage device configured to store energy and provide electrical energy to one or more system components. Example rechargeable energy storage devices include rechargeable batteries, capacitors (e.g., supercapacitors), or other appropriate components capable of receiving, storing, and delivering electrical energy.

The battery and/or communication module can be implanted, for example, into the pectoral region of the patient in order to provide adequate room for larger equipment (e.g., a relatively large battery) for prolonged operation (e.g., longer battery life). Additionally, in the event a rechargeable energy storage device such as an implanted battery needs eventual replacement, a replacement procedure in the patient's pectoral region can be performed several times without certain vascularization issues that can arise near the location of the cochlear implant. For example, in some cases, repeated procedures (e.g., battery replacement) near the cochlear implant can result in a decreased ability for the skin in the region to heal after a procedure. Placing a replaceable component such as a battery in the pectoral region can facilitate replacement procedures with reduced risk for such issues.

Figure 3:
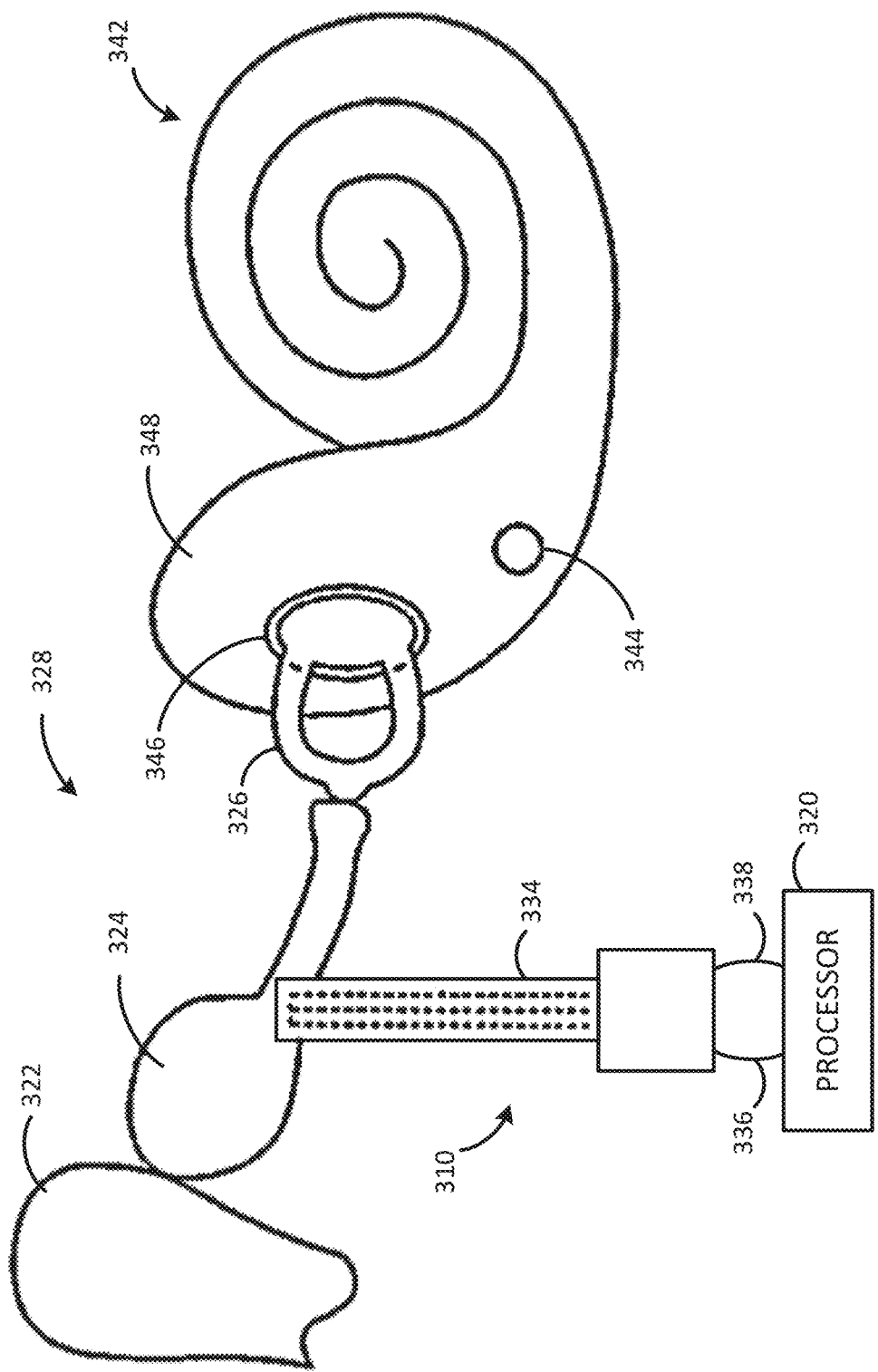
FIG. 3 illustrates an embodiments of an exemplary middle ear sensor for use in conjunction with anatomical features of a wearer.

FIG. 3 illustrates embodiments of an exemplary middle ear sensor for use in conjunction with anatomical features of a patient. Referring to FIG. 3, an embodiment of the sensor 310 of a fully-implantable cochlear implant is shown. Also shown are portions of the subject's anatomy, which includes, if the subject is anatomically normal, at least the malleus 322, incus 324, and stapes 326 of the middle ear 328, and the cochlea 348, oval window 346, and round window 344 of the inner ear 342. Here, the sensor 310 is touching the incus 324. The sensor 310 can include a sensor such as described in U.S. Patent Publication No. 2013/0018216, which is incorporated by reference. Further, although not shown in a drawing, the sensor 310 may be in operative contact with the tympanic membrane or the stapes, or any combination of the tympanic membrane, malleus 322, incus 324, or stapes 326.

FIG. 3 illustrates an exemplary middle ear sensor for use with systems described herein. However, other middle ear sensors can be used, such as sensors using microphones or other sensors capable of receiving an input corresponding to detected sound and outputting a corresponding signal to the signal processor. Additionally or alternatively, systems can include other sensors configured to output a signal representative of sound received at or near a user's ear, such as a microphone or other acoustic pickup located in the user's outer ear or implanted under the user's skin. Such devices may function as an input source, for example, to the signal processor such that the signal processor receives an input signal from the input source and generates and output one or more stimulation signals according to the received input signal and the signal processor transfer function. Additionally or alternatively, systems can include other types of sensors, such as inner ear sensors. Some example configurations of such systems and other sensor arrangements are described in PCT patent application No. PCT/US20/19166, which is incorporated by reference.

Referring back to FIG. 1, the signal processor 120 is shown as being in communication with the middle ear sensor 110, the electrical stimulator 130, and the implantable battery and/or communication module 140. As described elsewhere herein, the signal processor 120 can receive input signals from the middle ear sensor 110 and/or other input source(s) and output signals to the electrical stimulator 130 for stimulating the cochlear electrode 116. The signal processor 120 can receive data (e.g., processing data establishing or updating the transfer function of the signal processor 120) and/or power from the implantable battery and/or communication module 140.

In some embodiments, the implantable battery and/or communication module 140 can communicate with one or more external components, such as a programmer 100 and/or a charger 102. The charger 102 can wirelessly charge the rechargeable energy storage device in the implantable battery and/or communication module 140 when brought into proximity with the implantable battery and/or communication module 140 in the pectoral region of the patient. Such charging can be accomplished, for example, using inductive charging. The programmer 100 can be configured to wirelessly communicate with the implantable battery and/or communication module 140 via any appropriate wireless communication technology, such as Bluetooth, Wi-Fi, and the like. In some examples, the programmer 100 can be used to update the system firmware and/or software. In an exemplary operation, the programmer 100 can be used to communicate an updated signal processor 120 transfer function to the implantable battery and/or communication module 140. In various embodiments, the programmer 100 and charger 102 can be separate devices or can be integrated into a single device.

In the illustrated example of FIG. 1, the signal processor 120 is connected to the middle ear sensor 110 via lead 170. In some embodiments, lead 170 can provide communication between the signal processor 120 and the middle ear sensor 110. In some embodiments, lead 170 can include a plurality of isolated conductors providing a plurality of communication channels between the middle ear sensor 110 and the signal processor 120. The lead 170 can include a coating such as an electrically insulating sheath to minimize any conduction of electrical signals to the body of the patient. In various embodiments, one or more communication leads can be detachable such that communication between two components can be disconnected in order to electrically and/or mechanically separate such components. For instance, in some embodiments, lead 170 includes a detachable connector 171. Detachable connector 171 can facilitate decoupling of the signal processor 120 and middle ear sensor 110. Example detachable connectors are described in PCT patent application No. PCT/US20/19166, filed Feb. 21, 2020, which is assigned to the assignee of the instant application and is incorporated by reference. For example, with reference to FIG. 1, in some embodiments, lead 170 can include a first lead extending from the middle ear sensor 110 having one of a male or a female connector and a second lead extending from the signal processor 120 having the other of the male or female connector. The first and second leads can be connected at detachable connector 171 in order to facilitate communication between the middle ear sensor 110 and the signal processor 120.

In other examples, a part of the detachable connector 171 can be integrated into one of the middle ear sensor 110 and the signal processor 120. For example, in an exemplary embodiment, the signal processor 120 can include a female connector integrated into a housing of the signal processor 120. Lead 170 can extend fully from the middle ear sensor 110 and terminate at a corresponding male connector for inserting into the female connector of the signal processor 120. In still further embodiments, a lead (e.g., 170) can include connectors on each end configured to detachably connect with connectors integrated into each of the components in communication. For example, lead 170 can include two male connectors, two female connectors, or one male and one female connector for detachably connecting with corresponding connectors integral to the middle ear sensor 110 and the signal processor 120. Thus, lead 170 may include two or more detachable connectors.

Similar communication configurations can be established for detachable connector 181 of lead 180 facilitating communication between the signal processor 120 and the stimulator 130 and for detachable connector 191 of lead 190 facilitating communication between the signal processor 120 and the implantable battery and/or communication module 140. Leads (170, 180, 190) can include pairs of leads having corresponding connectors extending from each piece of communicating equipment, or connectors can be built in to any one or more communicating components.

In such configurations, each of the electrical stimulator 130, signal processor 120, middle ear sensor 110, and battery and/or communication module can each be enclosed in a housing, such as a hermetically sealed housing comprising biocompatible materials. Such components can include feedthroughs providing communication to internal components enclosed in the housing. Feedthroughs can provide electrical communication to the component via leads extending from the housing and/or connectors integrated into the components.

In a module configuration such as that shown in FIG. 1, various components can be accessed (e.g., for upgrades, repair, replacement, etc.) individually from other components. For example, as signal processor 120 technology improves (e.g., improvements in size, processing speed, power consumption, etc.), the signal processor 120 implanted as part of the system can be removed and replaced independently of other components. In an exemplary procedure, an implanted signal processor 120 can be disconnected from the electrical stimulator 130 by disconnecting detachable connector 181, from the middle ear sensor 110 by disconnecting detachable connector 171, and from the implantable battery and/or communication module 140 by disconnecting detachable connector 191. Thus, the signal processor 120 can be removed from the patient while other components such as the electrical stimulator 130, cochlear electrode 116, middle ear sensor 110, and battery and/or communication module can remain in place in the patient.

After the old signal processor is removed, a new signal processor can be connected to the electrical stimulator 130, middle ear sensor 110, and implantable battery and/or communication module 140 via detachable connectors 181, 171, and 191, respectively. Thus, the signal processor (e.g., 120) can be replaced, repaired, upgraded, or any combination thereof, without affecting the other system components. This can reduce, among other things, the risk, complexity, duration, and recovery time of such a procedure. In particular, the cochlear electrode 116 can be left in place in the patient's cochlea while other system components can be adjusted, reducing trauma to the patient's cochlear tissue.

Such modularity of system components can be particularly advantageous when replacing a signal processor 120, such as described above. Processor technology continues to improve and will likely continue to markedly improve in the future, making the signal processor 120 a likely candidate for significant upgrades and/or replacement during the patient's lifetime. Additionally, in embodiments such as the embodiment shown in FIG. 1, the signal processor 120 communicates with many system components. For example, as shown, the signal processor 120 is in communication with each of the electrical stimulator 130, the middle ear sensor 110, and the implantable battery and/or communication module 140. Detachably connecting such components with the signal processor 120 (e.g., via detachable connectors 181, 171, and 191) enables replacement of the signal processor 120 without disturbing any other components. Thus, in the event of an available signal processor 120 upgrade and/or a failure of the signal processor 120, the signal processor 120 can be disconnected from other system components and removed.

While many advantages exist for a replaceable signal processor 120, the modularity of other system components can be similarly advantageous, for example, for upgrading any system component. Similarly, if a system component (e.g., the middle ear sensor 110) should fail, the component can be disconnected from the rest of the system (e.g., via detachable connector 171) and replaced without disturbing the remaining system components. In another example, even a rechargeable battery or other rechargeable energy storage device included in the implantable battery and/or communication module 140 may eventually wear out and need replacement. The implantable battery and/or communication module 140 can be replaced or accessed (e.g., for replacing an energy storage device) without disturbing other system components. Further, as discussed elsewhere herein, when the implantable battery and/or communication module 140 is implanted in the pectoral region of the patient, such as in the illustrated example, such a procedure can leave the patient's head untouched, eliminating unnecessarily frequent access beneath the skin.

While various components are described herein as being detachable, in various embodiments, one or more components configured to communicate with one another can be integrated into a single housing. For example, in some embodiments, signal processor 120 can be integrally formed with the stimulator 130 and cochlear electrode 116. For example, in an exemplary embodiment, processing and stimulation circuitry of a signal processor 120 and stimulator 130 can be integrally formed as a single unit in a housing coupled to a cochlear electrode. Cochlear electrode and the signal processor/stimulator can be implanted during an initial procedure and operate as a single unit.

In some embodiments, while the integral signal processor/stimulator/cochlear electrode component does not get removed from a patient due to potential damage to the cochlear tissue into which the cochlear electrode is implanted, system upgrades are still possible. For example, in some embodiments, a modular signal processor may be implanted alongside the integral signal processor/stimulator component and communicate therewith. In some such examples, the integral signal processor may include a built-in bypass to allow a later-implanted signal processor to interface directly with the stimulator. Additionally or alternatively, the modular signal processor can communicate with the integral signal processor, which may be programmed with a unity transfer function. Thus, in some such embodiments, signals from the modular signal processor may be essentially passed through the integral signal processor unchanged so that the modular signal processor effectively controls action of the integral stimulator. Thus, in various embodiments, hardware and/or software solutions exist for upgrading an integrally attached signal processor that may be difficult or dangerous to remove.

While often described herein as using an electrical stimulator to stimulate the patient's cochlear tissue via a cochlear electrode, in some examples, the system can additionally or alternatively include an acoustic stimulator. An acoustic stimulator can include, for example, a transducer (e.g., a piezoelectric transducer) configured to provide mechanical stimulation to the patient's ear structure. In an exemplary embodiment, the acoustic stimulator can be configured to stimulate one or more portions of the patient's ossicular chain via amplified vibrations. Acoustic stimulators can include any appropriate acoustic stimulators, such as those found in the ESTEEM™ implant (Envoy Medical Corp., St. Paul, Minn.) or as described in U.S. Pat. Nos. 4,729,366, 4,850,962, and 7,524,278, and U.S. Patent Publication No. 20100042183, each of which is incorporated herein by reference in its entirety.

Figure 4:
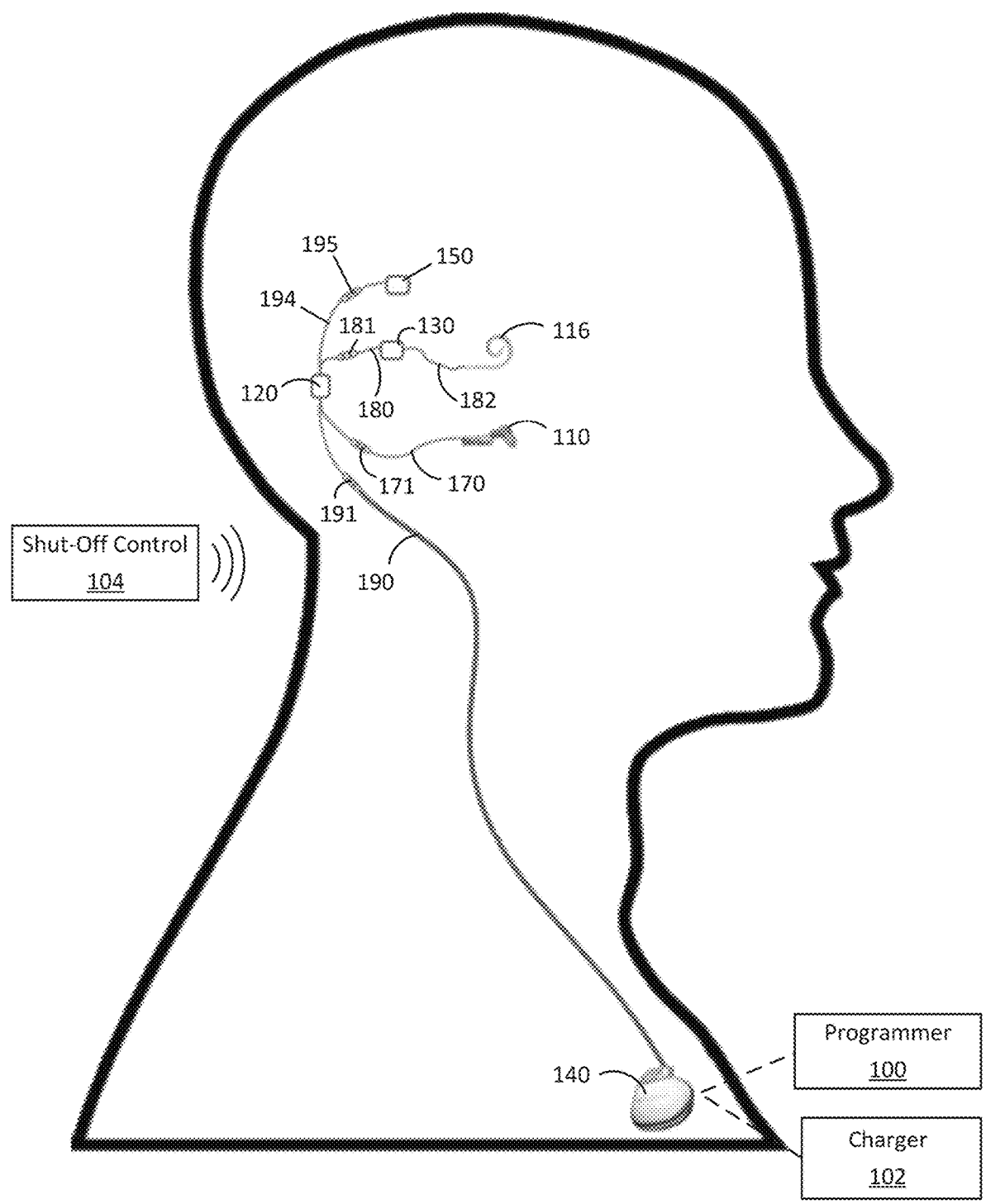
FIG. 4 is a schematic diagram illustrating an exemplary implantable system including an acoustic stimulator.

FIG. 4 is a schematic diagram illustrating an exemplary implantable system including an acoustic stimulator. The acoustic stimulator can be implanted proximate the patient's ossicular chain and can be in communication with a signal processor via lead 194 and detachable connector 195. The signal processor can behave as described elsewhere herein and can be configured to cause acoustic stimulation of the ossicular chain via the acoustic stimulator in in response to input signals from the middle ear sensor according to a transfer function of the signal processor.

The acoustic sensor of FIG. 4 can be used similarly to the electrical stimulator as described elsewhere herein. For instance, an acoustic stimulator can be mechanically coupled to a patient's ossicular chain upon implanting the system and coupled to the signal processor via lead 194 and detachable connector 195. Similarly to systems described elsewhere herein with respect to the electrical stimulator, if the signal processor requires replacement or repair, the signal processor can be disconnected from the acoustic stimulator (via detachable connector 195) so that the signal processor can be removed without disturbing the acoustic stimulator.

In general, systems incorporating an acoustic sensor such as shown in FIG. 4 can operate in the same way as systems described elsewhere herein employing an electrical stimulator and cochlear electrode only substituting electrical stimulation for acoustic stimulation.

Some systems can include a hybrid system comprising both an electrical stimulator and an acoustic stimulator in communication with the signal processor. In some such examples, the signal processor can be configured to stimulate electrically and/or acoustically according to the transfer function of the signal processor. In some examples, the type of stimulation used can depend on the input signal received by the signal processor. For instance, in an exemplary embodiment, the frequency content of the input signal to the signal processor can dictate the type of stimulation. In some cases, frequencies below a threshold frequency could be represented using one of electrical and acoustic stimulation while frequencies above the threshold frequency could be represented using the other of electrical and acoustic stimulation. Such a threshold frequency could be adjustable based on the hearing profile of the patient. Using a limited range of frequencies can reduce the number of frequency domains, and thus the number of contact electrodes, on the cochlear electrode. In other examples, rather than a single threshold frequency defining which frequencies are stimulated electrically and acoustically, various frequencies can be stimulated both electrically and acoustically. In some such examples, the relative amount of electrical and acoustic stimulation can be frequency-dependent. As described elsewhere herein, the signal processor transfer function can be updated to meet the needs of the patient, including the electrical and acoustic stimulation profiles.

With further reference to FIGS. 1 and 4, in some examples, a system can include a shut-off controller 104, which can be configured to wirelessly stop an electrical stimulator 130 from stimulating the patient's cochlear tissue and/or an acoustic stimulator 150 from stimulating the patient's ossicular chain. For example, if the system is malfunctioning or an uncomfortably loud input sound causes an undesirable level of stimulation, the user may use the shut-off controller 104 to cease stimulation from the stimulator 130. The shut-off controller 104 can be embodied in a variety of ways. For example, in some embodiments, the shut-off controller 104 can be integrated into other external components, such as the programmer 100. In some such examples, the programmer 100 includes a user interface by which a user can select an emergency shut-off feature to cease stimulation. Additionally or alternatively, the shut-off controller 104 can be embodied as a separate component. This can be useful in situations in which the patient may not have immediate access to the programmer 100. For example, the shut-off controller 104 can be implemented as a wearable component that the patient can wear at all or most times, such as a ring, bracelet, necklace, or the like.

The shut-off controller 104 can communicate with the system in order to stop stimulation in a variety of ways. In some examples, the shut-off controller 104 comprises a magnet that is detectable by a sensor (e.g., a Hall-Effect sensor) implanted in the patient, such as in the processor and/or the implantable battery and/or communication module 140. In some such embodiments, when the magnet is brought sufficiently close to the sensor, the system can stop stimulation of the cochlear tissue or ossicular chain.

After the shut-off controller 104 is used to disable stimulation, stimulation can be re-enabled in one or more of a variety of ways. For example, in some embodiments, stimulation is re-enabled after a predetermined amount of time after it had been disabled. In other examples, the shut-off controller 104 can be used to re-enable stimulation. In some such examples, the patient brings the shut-off controller 104 within a first distance of a sensor (e.g., a magnetic sensor) to disable stimulation, and then removes the shut-off controller 104. Subsequently, once the patient brings the shut-off controller 104 within a second distance of the sensor, stimulation can be re-enabled. In various embodiments, the first distance can be less than the second distance, equal to the second distance, or greater than the second distance. In still further embodiments, another device such as a separate turn-on controller (not shown) or the programmer 100 can be used to re-enable stimulation. Any combination of such re-enabling of stimulation can be used, such as alternatively using either the programmer 100 or the shut-off controller 104 to enable stimulation or combining a minimum "off" time before any other methods can be used to re-enable stimulation.

In some embodiments, rather than entirely disable stimulation, other actions can be taken, such as reducing the magnitude of stimulation. For example, in some embodiments, the shut-off sensor can be used to reduce the signal output by a predetermined amount (e.g., absolute amount, percentage, etc.). In other examples, the shut-off sensor can affect the transfer function of the signal processor to reduce the magnitude of stimulation in a customized way, such as according to frequency or other parameter of an input signal (e.g., from the middle ear sensor).

In some examples, implantable battery and/or communication module can be used to provide power and/or data (e.g., processing instructions) to other system components via lead 190. Different challenges exist for communicating electrical signals through a patient's body. For example, safety standards can limit the amount of current that can safely flow through a patient's body (particularly DC current). Additionally, the patient's body can act as an undesired signal path from component to component (e.g., via contact with the housing or "can" of each component). Various systems and methods can be employed provide communication between system components. Some examples of possible communication techniques are described in PCT patent application No. PCT/US20/19166, which is incorporated by reference. In some examples, data can be communicated to the implantable battery and/or communication module from an external component, such as a programmer as shown in FIG. 1. In an exemplary process, a programmer, such as a clinician's computer, can be used to communicate with a patient's fully implanted system via the implantable battery and/or communication module, which can communicate information to other system components, such as via lead 190.

During such processes, a clinician can communicate with the signal processor, and, in some cases, with other components via the signal processor. For example, the clinician can cause the signal processor to actuate an electrical and/or an acoustic stimulator in various ways, such as using various electrical stimulation parameters, combinations of active contact electrodes, various acoustic stimulation parameters, and various combinations thereof. Varying the stimulation parameters in real time can allow the clinician and patient to determine effectiveness of different stimulation techniques for the individual patient. Similarly, the clinician can communicate with the signal processor to update transfer function. For example, the clinician can repeatedly update the transfer function signal processor while testing the efficacy of each one on the individual patient. In some examples, combinations of stimulation parameters and signal processor transfer functions can be tested for customized system behavior for the individual patient.

In some embodiments, various internal properties of the system may be tested. For instance, various impedance values, such as a sensor impedance or a stimulator impedance can be tested such as described in U.S. Patent Publication No. 2015/0256945, entitled TRANSDUCER IMPEDANCE, MEASUREMENT FOR HEARING AID, which is assigned to the assignee of the instant application, the relevant portions of which are incorporated by reference herein.

While shown in several embodiments (e.g., FIGS. 1 and 4) as being separate components connected by a lead (e.g., lead 180), in some examples, the processor (e.g., 120) and the stimulator (e.g., 130) can be integrated into a single component, for example, within a hermetically sealed housing, as shown and discussed in PCT patent application No. PCT/US20/19166, which is incorporated by reference.

As described elsewhere herein, while many examples show a middle ear sensor being in communication with an implanted signal processor, in various embodiments, one or more additional or alternative input sources can be included. For instance, in some embodiments, a microphone can be implanted under a user's skin and can be placed in communication with the signal processor (e.g., via a detachable connector such as 171). The signal processor can receive input signals from the implanted microphone and provide signals to the stimulator based on the received input signal and the signal processor transfer function.

As described, in some embodiments, a rechargeable energy storage device (e.g., a rechargeable battery, capacitor, or the like) in the implantable battery and/or communication module 140 can provide electrical power to one or more system components, but may ultimately require recharging. However, in some examples, recharging the device can cause one or more components of the implantable battery and/or communication module to heat. For example, a battery (e.g., a lithium-ion battery) can increase in temperature during charging. Additionally or alternatively, an electromagnetic field created by an external charging coil can induce currents (e.g. eddy currents) within a housing of the implantable battery and/or communication module (e.g., a titanium can including a rechargeable battery). Such induced currents can cause the can to increase in temperature (e.g., via resistive heating).

Many medical device standards dictate how much and to what extent, if at all, implanted medical devices can increase in temperature. For example, some standards mandate that under normal operating conditions, implanted medical devices shall not exceed 2.0° C. greater than the surrounding tissue temperature (e.g. 37° C.) for longer term exposures. Some alternative models of thermal injury thresholds have been developed to consider acute exposure durations in order to address shorter term exposures such as MRI procedure and inductive recharge. One example is a CEM43 (cumulative equivalent minutes at 43° C.) quantification, which accounts for a temperature and time component of thermal exposure/thermal dose to surrounding tissue. The CEM43 quantification normalizes a thermal dose to a common temperature (43° C.) so that thermal doses applied at different temperatures can be compared to a consistent standard more easily.

CEM43 can be calculated via an integral as shown in Equation (1)

$$CEM43 = \int_0^t (R^{43-T_m}) dt \quad (1)$$

Where $R=0.25$ for $T_m<43$ and $R=0.5$ for $T_m>43$.

In some cases, for components implanted in human tissue, temperatures of over 43° C. are not practical, so a value of $R=0.25$ can be used. Moreover, the integral of Equation (1) can be approximated as a summation using discrete periodic temperature measurements. Equation (2) shows a CEM43 approximation using $R=0.25$ and discrete temperature measurements over time.

$$CEM43 = \Sigma \Delta Time \cdot 0.25^{43-T_m} \quad (2)$$

Figure 5:
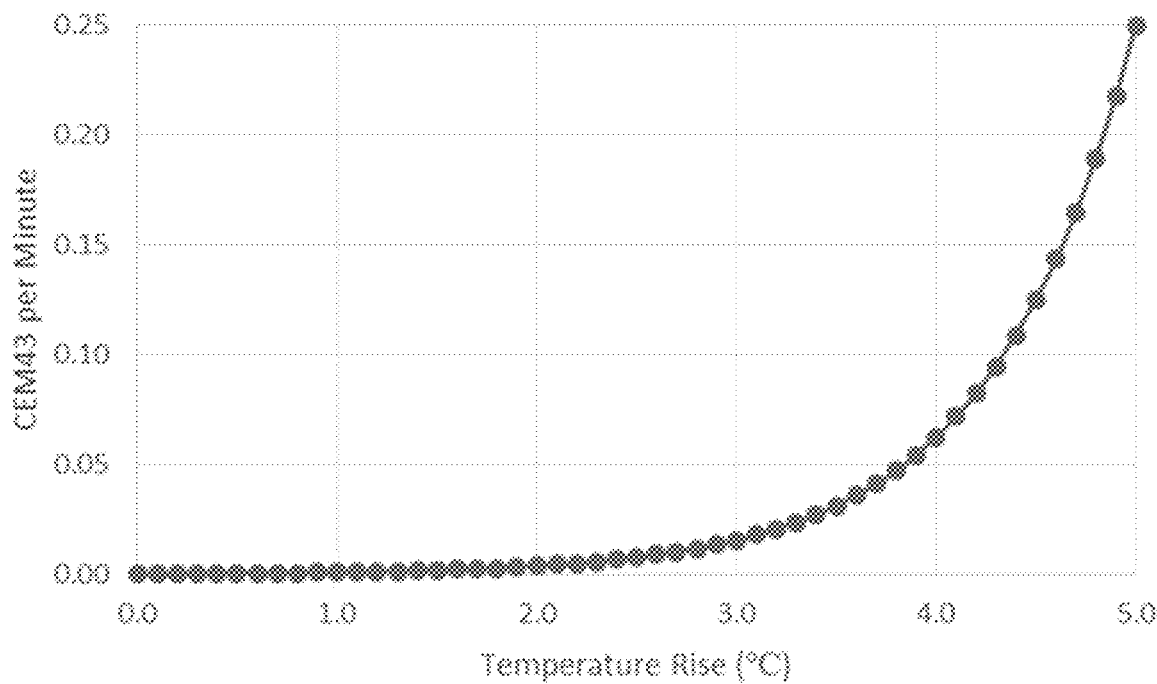
FIG. 5 illustrates an exemplary relationship between CEM43 and temperature rise.

FIG. 5 shows a graph of CEM43 per minute as a function of a temperature rise above body temperature (37° C.). As shown, as temperature increases beyond 2.0° C. above body temperature, the CEM43 accumulated per minute begins to increase rapidly compared to temperatures below 39° C. A temperature rise of 6° C. above 37° C. (corresponding to a temperature of 43° C.) would have a CEM43 accumulation per minute of 1.0.

Various CEM43 exposure safety limits apply to different types of tissue, for example, according to section 17 of ISO 14708-7. In some examples, a maximum CEM43 value can be set according to the placement of the battery or other rechargeable energy storage device being charged. For example, bone has a limit of CEM43=16, and in some cases, to ensure safe operation, a CEM43 limit of 15 can be used.

In some cases, when performing various tasks, such as induction charging, the process may proceed for longer than 15 minutes, and in some examples, can last for one or more hours. As shown in FIG. 5, the CEM43 function is nonlinear and there is very little contribution at low temperate rises, such as temperatures relatively close to 37° C. Conversely, as the temperature rises further (e.g. away from 37° C.), the CEM43 per minute may go up at an exponential rate.

Various components comprised within an implantable cochlear implant system as described herein may require power to perform properly. In some embodiments, that power may be supplied by one or more implantable rechargeable energy storage devices, such as a battery comprised within an implantable battery and/or communication module. However, as described, the rechargeable energy storage device may need to be periodically charged, such as via an external charger, in order to continue providing power to various components.

In some situations, it may be beneficial to quickly charge the rechargeable energy storage device. For instance, shorter charging times may be more convenient for a wearer compared to waiting for such a rechargeable device to charge over a long period of time. However, charging the rechargeable energy storage device more quickly can result in more heat generated by the device, the charger, or induced in surrounding components/housings. Such heat may, in some situations, reach unsafe temperature and/or breach safety regulations (e.g. CEM43) as discussed above. For example, in some cases, because of the nonlinear increase in thermal dose at higher temperatures, larger charging currents that result in larger temperature increases may increase the temperature to the point that a thermal dose limit is reached before a full charge.

Figure 6:
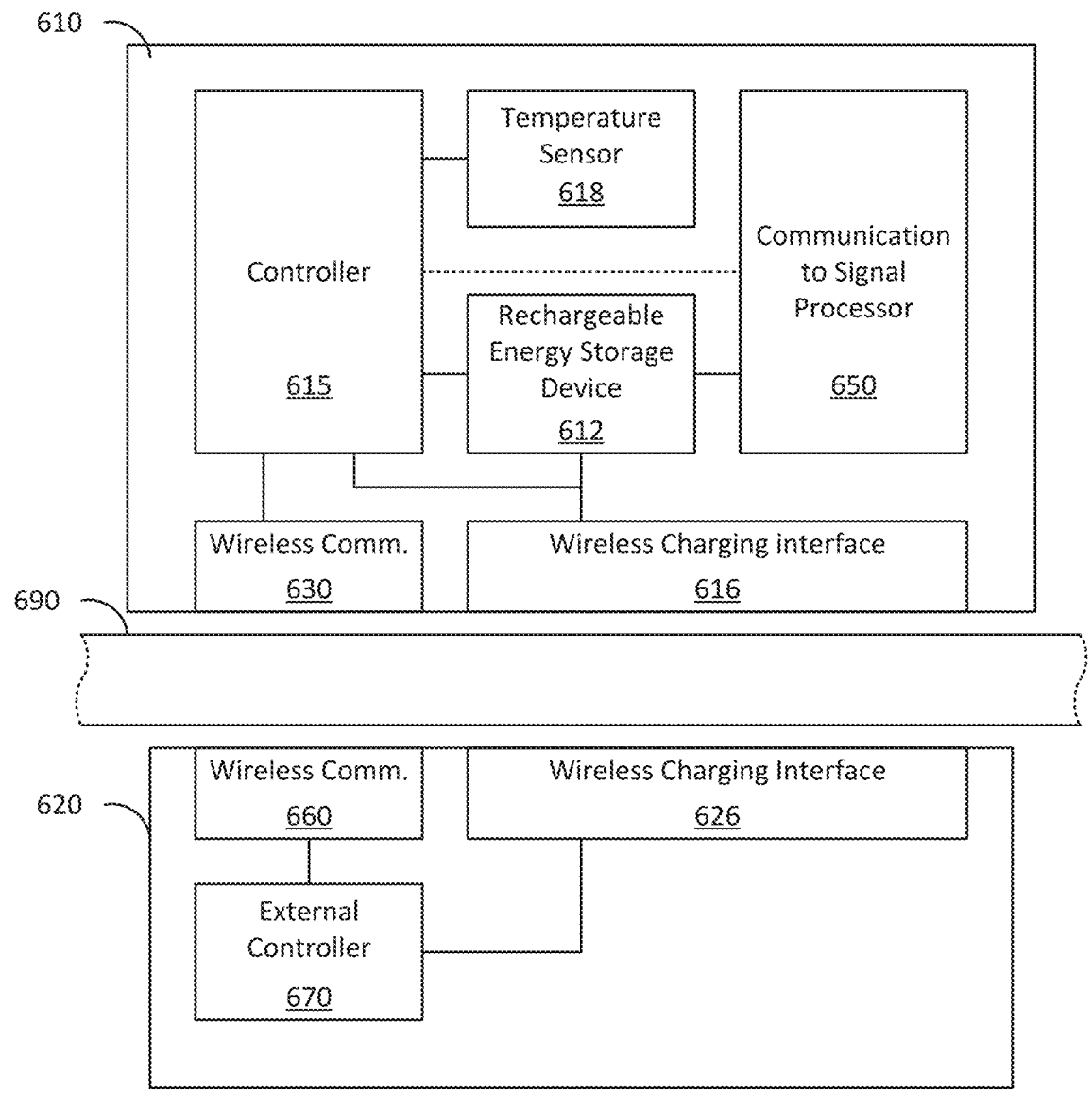
FIG. 6 shows a schematic illustration of an implantable battery and/or communication module and a charger.

FIG. 6 provides an exemplary illustration of a charger configured to charge an implantable battery and/or communication module through a wearer's skin. As described elsewhere herein, the implantable battery and/or communication module 610 may be configured to provide electrical power to one or more implanted system components such as a cochlear electrode, a stimulator, a sensor, a signal processor. A charger 620 and implantable battery and/or communication module 610 may interface with one another to charge a rechargeable energy storage device 612 (e.g. a rechargeable battery). In some examples, charging can be performed at an optimized rate (e.g. optimized current) while still meeting medical and safety standards. In some embodiments, implantable battery and/or communication module 610 of FIG. 6 can be included as a part of a cochlea implant system such as those described herein.

The implantable battery and/or communication module 610 of FIG. 6 comprises a rechargeable energy storage device 612, a temperature sensor 618, and a first wireless charging interface 616. The rechargeable energy storage device 612 may be configured to provide power to various implantable components as described herein. The temperature sensor 618 may be configured to measure the temperature of the implantable battery and/or communication module 610 and/or the surrounding environment. For example, in various embodiments, the temperature sensor 618 can be configured to detect a temperature of the rechargeable energy storage device 612, a can/housing, of the implantable battery and/or communication module 610, or an environment within the implantable battery and/or communication module 610. Any appropriate temperature sensor can be used, for example, a thermocouple, thermistor, thermopile, infrared sensor, or the like.

The first wireless charging interface 616 may be used to charge the rechargeable energy storage device 612, for example, via wirelessly receiving power from an external source. In some embodiments, the first wireless charging interface 616 may comprise a coil. Additionally or alternatively, in some embodiments, wireless charging interface 616 can include an antenna. In some embodiments, an antenna can facilitate far field communication and/or power transmission from an external source to the rechargeable energy storage device 612.

In the example of FIG. 6, the implantable battery and/or communication module 610 comprises an implantable controller 615. The implantable controller 615 may be in communication with one or more components of the implantable battery and/or communication module 610, such as the rechargeable energy storage device 612, the temperature sensor 618, the first wireless charging interface 616, or the like. In some embodiments, the implantable controller 615 comprises a digital signal processor, one or more microprocessors, microcontrollers, application specific integrated circuits (ASICs) or the like. Supporting circuitry for one or more such components can also be included as a part of the implantable controller 615. In some embodiments, the signal processor can include or otherwise communicate with a memory containing programming for operating one or more components.

Charger 620 may comprise a second wireless charging interface 626, such as a coil. In some embodiments, the second wireless charging interface 626 may be configured to interface with the first wireless charging interface 616 and cause first wireless charging interface 616 to provide an electrical current to rechargeable energy storage device 612. For example, in some embodiments, second wireless charging interface 626 comprises a coil and can induce a current in a coil within the first wireless charging interface 616.

The charger 620 may further comprise an external controller 670. The external controller 670 may be in communication with one or more components of the charger 620, such as the second wireless charging interface 626. In some embodiments, the external controller 670 comprises a digital signal processor, one or more microprocessors, microcontrollers, application specific integrated circuits (ASICs) or the like. Supporting circuitry for one or more such components can also be included as a part of the external controller 670. In some embodiments, the signal processor can include or otherwise communicate with a memory containing programming for operating one or more components. In some embodiments, the implantable controller 615 may be in wireless communication with the implantable controller 615, such as via one or more wireless communication interfaces 630, 660.

Figure 7:
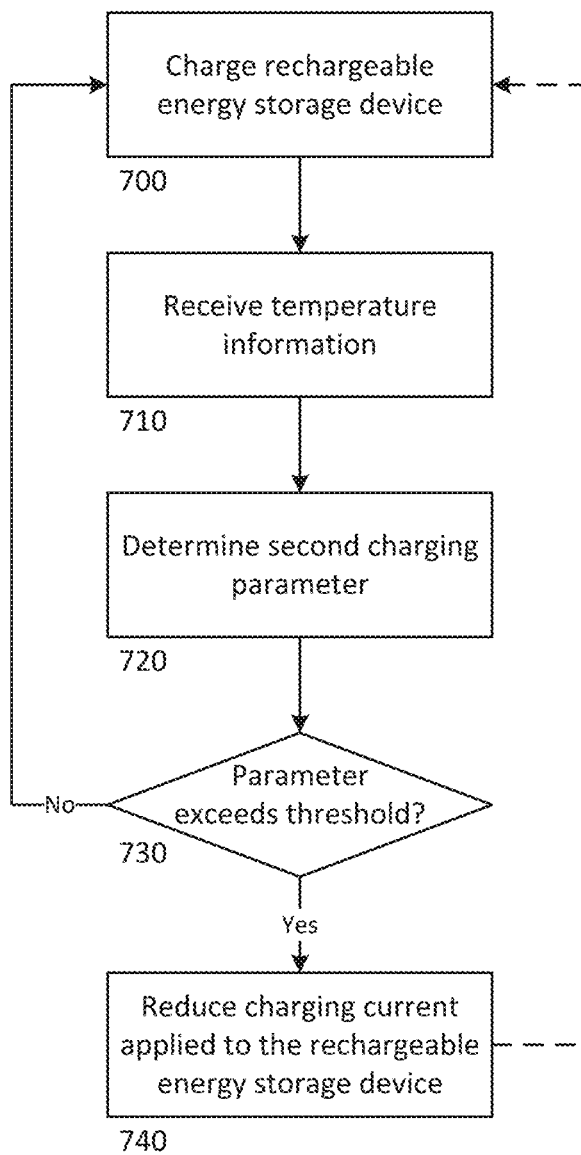
FIG. 7 shows a first exemplary method of charging a rechargeable energy storage device.

FIG. 7 provides an exemplary method of how an implantable battery and/or communication module may be charged while still meeting medical and safety standards. As shown, the method may comprise an initial step 700 of charging the rechargeable energy storage device (e.g. 612). In some embodiments, charging may comprise receiving energy at the rechargeable energy storage device via the first wireless charging interface (e.g., 616) and providing an electrical current to the rechargeable energy storage device therefrom. Charging (step 700) may comprise charging the rechargeable energy storage device using a set of charging settings. The charging settings may comprise an amount of electrical current provided to charge the rechargeable energy storage device, an amount of time to charge the rechargeable energy storage device, or the like. The method may further comprise receiving temperature information representative of a temperature in and/or around the implantable battery and/or communication module 610 at a first time (Step 710). In some embodiments, temperature information may be received by a temperature sensor, such as temperature sensor 618. The method may further comprise determining a second charging parameter associated with the charging of the rechargeable energy storage device (step 720). The second charging parameter may comprise a variety of different values, such as an amount of time the rechargeable energy storage device has been charging, an among of current being provided to the rechargeable energy storage device, or the like.

The method may further comprise comparing a parameter associated with charging the rechargeable energy storage device to a corresponding threshold (Step 730). In some embodiments, the parameter analyzed in step 730 may comprise the second charging parameter or the received temperature information. As shown in FIG. 7, if the parameter does not exceed the corresponding threshold (e.g. NO in Step 730) the method may proceed with charging the rechargeable energy storage device using the set of charging settings (Step 700). However, if the parameter exceeds the corresponding threshold (e.g. YES in Step 730) the method includes adjusting the charging settings (Step 740) before continuing to charge the rechargeable energy storage device (Step 700). In the illustrated example, adjusting the charging settings in response to the parameter exceeding the corresponding threshold in step 730 includes reducing the amount of electrical current provided to the rechargeable energy storage device during charging. In some embodiments, reducing the amount of electrical current provided may comprise stopping the charging of the rechargeable energy storage device.

In some embodiments, the method described in FIG. 7 may be performed by one or more controllers or processors, such as the implantable controller 615, the external controller 670, or a combination thereof. For example, all or a portion of the method discussed with respect to FIG. 7 may be performed by the external controller 670. In such embodiments, temperature information may be received by the implantable controller 615 (e.g. via temperature sensor 618) and the implantable battery and/or communication module 610 may communicate the temperature information and the second charging parameter to the external controller 670, such as via a wireless connection (e.g. via one or more wireless communication interfaces 630, 660). In another example, an implantable controller can be configured to generally perform the steps shown in FIG. 7. In some such examples, the implantable controller can cause a reduction in charging current applied to the rechargeable energy storage device by instructing an external charger to reduce the applied current (e.g., via wireless communication interface 630 and 660). Reducing the applied current can include, in some embodiments, reducing an applied field strength in order to reduce an induced current via a wireless charging interface. Additionally or alternatively, in some embodiments, reducing the applied current can include manipulating one or more wireless charging interfaces (e.g., 616 and/or 626 in FIG. 6). For example, in some cases, reducing the applied current can include detuning one or more coils (e.g., a coil associated with wireless charging interface 616 of the implantable battery and/or communication module 610) in order to reduce the amount of current induced by the wireless communication.

Figure 8:
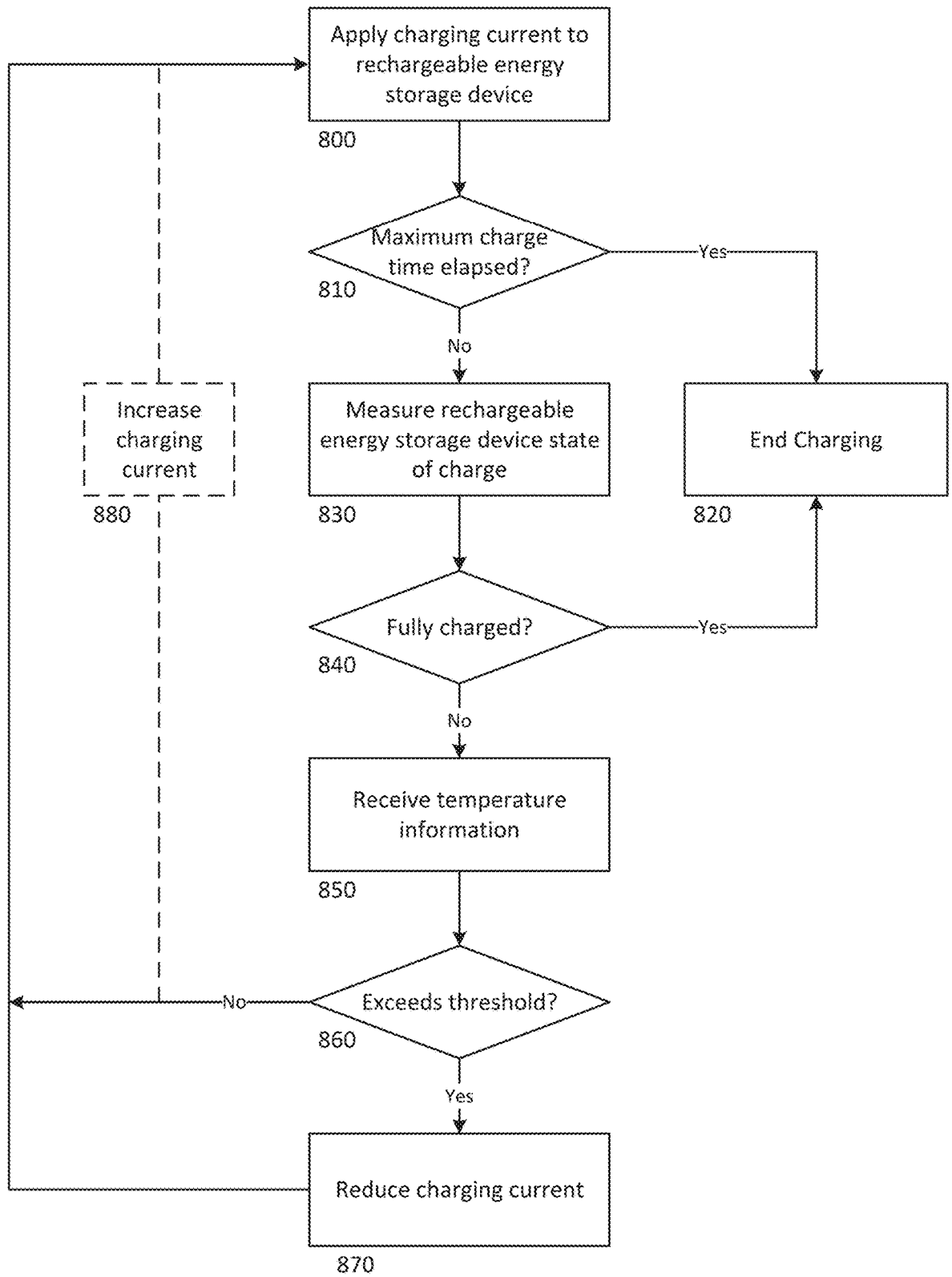
FIG. 8 shows a second example method of charging a rechargeable energy storage device.

FIG. 8 provides an exemplary method of how an implantable battery and/or communication module may be charged while still meeting medical and safety standards. The method of FIG. 8 may comprise an initial step of charging the rechargeable energy storage device (Step 800). As described herein, charging the rechargeable energy storage device may comprise charging the rechargeable energy storage device using a set of charging settings. Furthermore, the method shown in FIG. 8 comprises determining whether a maximum charge time has elapsed (Step 810). In some embodiments, the maximum charge time may be a predetermined value, such as 30 minutes, 1 hour, or the like. Additionally or alternatively, the maximum charging time may be based on various parameters such as the age of the rechargeable energy storage device, the power/current being used to charge the rechargeable energy storage device, the type/size of the rechargeable energy storage device, the temperature of or around the rechargeable energy storage device, or the like.

In some embodiments, if the maximum charge time has elapsed (e.g. YES in Step 810), the method may proceed to ending the charging process (Step 820). Conversely, if the maximum charge time has not elapsed (e.g. NO in Step 810), the method may proceed to measure the state of charge of the rechargeable energy storage device (Step 830). Measuring the state of charge may comprise measuring a voltage associated with the rechargeable energy storage device and correlating the voltage to a state of charge, for example, via a lookup table stored in memory. Additionally or alternatively, current provided to and from the rechargeable energy storage device can be monitored over time to track the state of charge. In some embodiments, a coulomb counter can be used to track a state of charge.

The method may further comprise determining whether the rechargeable energy storage device is fully charged, (Step 840), such as based on the measured state of charge. In some examples, a fully charged rechargeable energy storage device is associated with a predetermined voltage level (e.g., 4.1 V for certain Li-ion batteries). In some embodiments, if the rechargeable energy storage device is fully charged (e.g. YES in Step 840), the method may proceed to ending the charging process (Step 820). With respect to Step 840, in some embodiments, determining whether the rechargeable energy storage device is fully charged can include determining whether the rechargeable energy storage device is charged to or above a threshold state of charge (e.g., 100%, 95%, or the like). In some examples, the state of charge corresponding to "fully charged" can be designated by a user and/or during manufacturing.

As discussed herein, if the rechargeable energy storage device is not fully charged (e.g. NO in Step 840), the method may proceed to receiving temperature information associated with a temperature of the implantable battery and/or communication module (Step 850). As discussed with respect to Step 710, temperature information may be received by a temperature sensor, such as temperature sensor 618, and can indicate a temperature of a rechargeable energy storage device, the implantable battery and/or communication module can, or the like. The temperature information may additionally be compared to a threshold to see whether it exceeds a threshold (Step 860).

If the temperature does not exceed the temperature threshold (e.g. NO in Step 860) the method may proceed with charging the rechargeable energy storage device using the set of charging settings (Step 800). However, if the temperature exceeds the corresponding threshold (e.g. YES in Step 860) the method may proceed with adjusting the charging settings, such as reducing the charging current (Step 870) before continuing to charge the rechargeable energy storage device (Step 800). In some embodiments, adjusting the charging settings may comprise reducing the amount of electrical current provided to the rechargeable energy storage device during charging. In some embodiments, reducing the amount of electrical current provided may comprise stopping the charging of the rechargeable energy storage device.

In some embodiments, after reducing charging current (as in Step 870), the reduced charging current can be applied to the rechargeable energy storage device (Step 800) until the received temperature information no longer exceeds a threshold (as in Step 860). In some embodiments, when the temperature decreases below the threshold, the charging current can be increased (as in step 880) in order to increase charging speed while remaining at a safe temperature. For example, in some cases, if the temperature information falls below the threshold, the charging current can be increased to the initial charging current.

Accordingly in some embodiments, a system can, during charging, monitor the amount of time that has elapsed and a temperature associated with the charging rechargeable energy storage device (e.g., the temperature of the can of the implantable battery and/or communication module). Both the amount of time and the temperature can be compared to corresponding thresholds. If the temperature exceeds a threshold temperature, the charging current can be reduced so that the temperature decreases below the threshold temperature. Similarly, if the time exceeds the threshold duration, charging can be stopped.

In some examples, the temperature threshold and charging duration threshold are such that, if the temperature were maintained at the threshold temperature for the threshold duration, the total thermal dose would be at or below a predetermined level. Accordingly, maintaining a temperature below the threshold and/or a duration below the threshold guarantees the total thermal dose will be below such a predetermined level at the conclusion of charging.

In some examples, when using the charge control process of FIG. 8, charging begins by applying a maximum current value, such as a maximum current deliverable by the system and/or a predefined maximum, such as set by a clinician to comply with safety standards. For example, in some embodiments, current is limited to a C/2 rate, meaning the level of current that will provide one half the capacity of the battery in one hour. Some such charging limits can correspond to certain charge storage technologies, such as limiting to a C/2 current in embodiments comprising a lithium-ion battery. In other examples, the maximum charge rate can be higher than a C/2 rate, for example, in embodiments using one or more capacitors (e.g., supercapacitors) for charge storage.

In some examples, the default charging setting comprises charging the rechargeable energy storage device as quickly as possible (e.g., at a maximum charge rate associated with the embodiment), and the current is reduced (e.g., in step 870) to accommodate for safety standards if the temperature exceeds a threshold in step 860. As described elsewhere herein, in some cases, the current can be increased from the reduced level back to the maximum current if the temperature falls below the threshold.

In some examples, methods similar to that shown in FIG. 8 can be included within the process shown in FIG. 7. For example, with respect to FIG. 7, the second charging parameter can include a charging duration, and determining whether a parameter exceeds a threshold in step 730 can include determining whether temperature information or a charging duration exceed a corresponding threshold.

Figure 9:
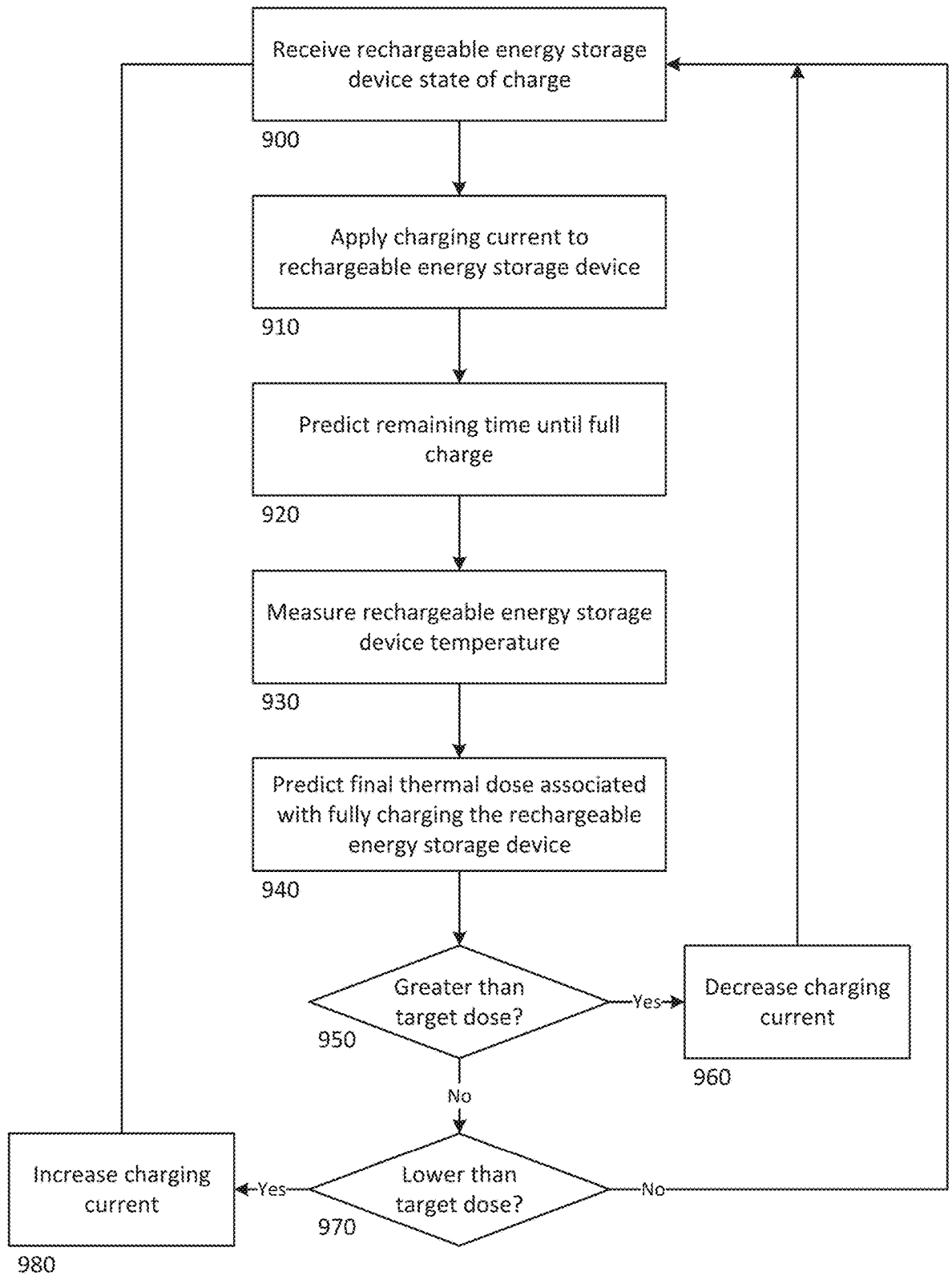
FIG. 9 shows a third example method of charging a rechargeable energy storage device.

FIG. 9 provides another exemplary method of how an implantable battery and/or communication module may be charged while still meeting medical and safety standards. As shown, the initial method step may comprise receiving the state of charge of an implantable rechargeable energy storage device (e.g. 612). The method may further comprise charging the rechargeable energy storage device using a set of charging settings, such as by applying a charging current thereto (step 910). Furthermore, the method may further include the step of predicting the remaining time until the rechargeable energy storage device is fully charged (Step 920). As described elsewhere herein, in some embodiments, a fully charge state does not necessarily correspond to a maximum possible charge on the rechargeable energy storage device. Rather, fully charged can refer to a predefined amount of charge (e.g., 95% of maximum charge capacity or the like).

Predicting the remaining time until full charge may be based on received state of charge information (e.g. step 910) as well as the set of charging settings (e.g. the charging current). In such embodiments, the state of charge and the charging current may be used to calculate the time remaining until the rechargeable energy storage device achieves a full charge, for example, via an equation or lookup table.

Furthermore, the method of FIG. 9 may comprise predicting a thermal dose associated with charging the rechargeable energy storage device to a fully charged state based on the received temperature information and the predicted amount of time remaining until the rechargeable energy storage device is fully charged (step 940). In various examples, such predictions can be made using an equation and/or a lookup table stored in memory. In some embodiments, step 940 comprises predicting a CEM43 value associated with fully charging the rechargeable energy storage device. In some such examples, a CEM43 equation (e.g., Equations 1 or 2 above) or lookup table (e.g., including data similar to that shown in FIG. 5). Other cumulative thermal dose values may be used in addition to or alternatively to CEM43.

The method may further comprise determining whether the predicted thermal dose value is greater than a target dose (e.g. Step 950). If the predicted thermal dose value exceeds the target dose (e.g. YES in Step 950), the method may proceed with adjusting the set of charging settings, for example, decreasing the charging current (step 960). Reducing the current can lower the temperature and overall thermal dose associated with charging the rechargeable energy storage device.

In the embodiment of FIG. 9, if the predicted thermal dose value is greater than the target dose in step 970, charging may continue at the given charging rate. However, if the predicted thermal dose value does not exceed the target dose (e.g. NO in step 950), the method may proceed to determining whether the predicted thermal dose value is lower than the target dose (e.g. Step 970). If the predicted thermal dose value is lower than the target dose value (e.g. YES in Step 970) the method may proceed to adjusting the set of charging settings, such as by increasing the charging current (step 980). That is, in some examples, if the predicted thermal dose is below a target value, there can be room to increase the current (and likely resulting temperature and thermal dose associated with a full charge) while keeping the overall thermal dose to safe levels. Thus, charging time can be reduced while maintaining safety.

In some embodiments, after the charging rate is adjusted (e.g. increased, decreased) or kept the same, the method may continue with step 900 as shown in FIG. 9. However, alternative methods may comprise reverting back to other steps or comprise waiting an amount of time prior to cycling threw the process again.

In some embodiments, the target dose referenced in step 950 and the target dose referenced in step 970 are the same target dose value. Such a target dose can include a preset thermal dose a maximum safe CEM43 value) for charging the rechargeable energy storage device. In some embodiments, such a preset thermal dose can be programmed by a clinician or wearer, though in some examples, a preset thermal dose selectable by a wearer is prevented from exceeding a maximum value to prevent unsafe operation.

In some examples, the target dose corresponds to a range of thermal dose values (e.g., a range of CEM43 values) deemed acceptable for charging. In some such examples, determining whether the thermal dose is greater than the target dose in step 950 comprises comparing the determined thermal dose to an upper limit of the range of thermal dose values. Similarly, in some such examples, determining whether the thermal dose is lower than the target dose in step 970 comprises comparing the determined thermal dose to a lower limit of the range of thermal dose values. Accordingly, in some such examples, is the predicted thermal dose associated with charging the rechargeable energy storage device is above or below a predetermine range of values, the system can adapt by decreasing or increasing the charging current, respectively. This allows the system to charge the rechargeable energy storage device at a maximum rate while maintaining a safe total thermal dose associated with charging.

Similar to FIG. 8 discussed above, in some examples, methods similar to that shown in FIG. 9 can be included within the process shown in FIG. 7. For example, with respect to FIG. 7, the second charging parameter can include a thermal dose (e.g., a CEM43 value), and determining whether a parameter exceeds a threshold in step 730 can include determining whether the thermal dose exceeds a target thermal dose value.

While generally described and shown herein with respect to cochlear implant systems, charging systems and methods described herein for quickly and safely charging an implanted rechargeable energy storage device can be used in a variety of systems. For instance, charging systems and methods described herein can be used in any medical device having an implanted rechargeable energy storage device. Such systems and methods can be used to limit the thermal dose to the tissue surrounding the rechargeable energy storage device to safe levels during charging processes.

Various non-limiting embodiments have been described. These and others are within the scope of the following enumerated embodiments.

The invention claimed is:
1. A system comprising:
an implantable device, the implantable device comprising:
 a rechargeable energy storage device;
 a temperature sensor proximate the rechargeable energy storage device and being configured to output temperature information representative of a temperature value proximate the rechargeable energy storage device;
 a wireless charging interface configured to wirelessly receive electrical energy and provide current to the rechargeable energy storage device; and
a controller configured to, while the rechargeable energy storage device is charging via the wireless charging interface:
 (a) receive the temperature information from the temperature sensor;
 (b) receive or determine an amount of current being provided to the rechargeable energy storage device from the wireless charging interface during charging;
 (c) determine a state of charge of the rechargeable energy storage device;
 (d) predict a cumulative thermal dose associated with charging the rechargeable energy storage device to a fully charged state based on the received temperature information, the determined state of charge of the rechargeable energy storage device, and the determined amount of current being applied to the rechargeable energy storage device;
 (e) compare a parameter associated with charging the rechargeable energy storage device to a corresponding threshold; and

(f) if the parameter associated with the charging the rechargeable energy storage device exceeds the corresponding threshold, reduce the amount of current provided to the rechargeable energy storage device during charging.

2. The system of claim 1, wherein:
the comparing the parameter associated with charging the rechargeable energy storage device to the corresponding threshold in step (e) comprises comparing the received temperature information to a temperature threshold.

3. The system of claim 1, wherein predicting the cumulative thermal dose associated with charging the rechargeable energy storage device to the fully charged state comprises determining a predicted cumulative equivalent minutes at 43° C. (CEM43) value associated with charging the rechargeable energy storage device to the fully charged state.

4. The system of claim 3, wherein the controller is configured to:
compare the predicted CEM43 value to a target value or range of values; and
adjust the amount of current applied to the rechargeable energy storage device if the if the predicted CEM43 value is above or below the target value or range of values; wherein
adjusting the amount of current applied to the rechargeable energy storage device if the predicted CEM43 value is above or below the target value or range of values comprises:
if the predicted CEM43 value is greater than the target value or range of values, decreasing the amount of current applied to the rechargeable energy storage device; and
if the predicted CEM43 value is less than the target value or range of values, increasing the amount of current applied to the rechargeable energy storage device.

5. A system comprising:
an implantable battery and/or communication module configured to provide electrical power to one or more implanted system components, the implantable battery and/or communication module comprising, a rechargeable energy storage device, a temperature sensor, and a first wireless charging interface; and
a controller configured to, while the rechargeable energy storage device is charging:
receive temperature information representative of a temperature in the implantable battery and/or communication module at a first time;
receive or determine an amount of current being provided to the rechargeable energy storage device during charging;
receive state-of-charge information representative of a charge of the rechargeable energy storage device;
predict an amount of time remaining until the rechargeable energy storage device is fully charged based on the received state-of-charge information and the amount of current being provided to the rechargeable energy storage device during charging;
predict a cumulative thermal dose associated with charging the rechargeable energy storage device to a fully charged state based on the received temperature information and the predicted amount of time remaining until the rechargeable energy storage device is fully charged;
compare a parameter associated with charging the rechargeable energy storage device to a corresponding threshold; and
if the parameter associated with charging the rechargeable energy storage device exceeds the corresponding threshold, reduce the amount of current provided to the rechargeable energy storage device during charging.

6. The system of claim 5, wherein the rechargeable energy storage device comprises a lithium-ion battery.

7. The system of claim 5, wherein:
the controller comprises an external controller; and
the implantable battery and/or communication module comprises a wireless communication interface and an implanted controller configured communicate the temperature information and the amount of current being provided to the rechargeable energy storage device during charging to the external controller via the wireless communication interface.

8. The system of claim 5, wherein the comparing the parameter associated with the charging of the rechargeable energy storage device to the corresponding threshold comprises comparing the temperature represented by the temperature information to a temperature threshold such that, if the temperature exceeds the temperature threshold, the controller is configured to reduce the amount of current provided to the rechargeable energy storage device during charging.

9. The system of claim 8, wherein the controller is further configured to, if, after reducing the amount of current provided to the rechargeable energy storage device, the temperature represented by the temperature information decreases below the temperature threshold, increase the amount of current provided to the rechargeable energy storage device during charging.

10. The system of claim 5, wherein the comparing the parameter associated with charging the rechargeable energy storage device to the corresponding threshold comprises comparing the predicted cumulative thermal dose associated with charging the rechargeable energy storage device to the fully charged state to a thermal dose threshold.

11. The system of claim 5, comprising a cochlear implant system comprising:
a cochlear electrode;
a stimulator in electrical communication with the cochlear electrode;
a sensor configured to receive a stimulus signal and generate an input signal based on the received stimulus signal; and
a signal processor in communication with the stimulator and the sensor, the signal processor being programmed with a transfer function and being configured to:
receive the input signal from the sensor; and
output a stimulation signal to the stimulator based on the received input signal and the transfer function; and wherein
the implantable battery and/or communication module is configured to provide electrical power to the signal processor.

12. The system of claim 5, wherein the predicted cumulative thermal dose comprises a cumulative equivalent minutes at 43° C. (CEM43) value.

13. The system of claim 12, wherein the controller is further configured to:
compare the predicted CEM43 value to a target CEM43 value or range of values; and if the predicted CEM43 value is greater than the target CEM43 value or range of values, decrease the amount of current provided to the rechargeable energy storage device.

14. The system of claim 13, wherein the controller is further configured to, if the predicted CEM43 value is less than the target CEM43 value or range of values, increase the amount of current provided to the rechargeable energy storage device.

15. The system of claim 13, wherein the controller is configured to:
receive updated temperature information representative of a temperature in the implantable battery and/or communication module at a second time, the second time being later than the first time;
update the predicted CEM43 value based on the updated temperature information; and
adjust a current being applied to the rechargeable energy storage device based on the updated predicted CEM43 value if the updated predicted CEM43 value meets a predetermined condition.

16. The system of claim 15, wherein the controller is configured to periodically receive updated temperature information representative of a temperature in the implantable battery and/or communication module, update the predicted CEM43 value based on the received updated temperature information, and adjust the current being applied to the rechargeable energy storage device based on the updated predicted CEM43 value if the updated predicted CEM43 value meets the predetermined condition.

17. The system of claim 16, wherein periodically receiving updated temperature information comprises receiving updated temperature information at least once per minute.

18. The system of claim 15, wherein the adjusting the current being applied to the rechargeable energy storage device based on the updated predicted CEM43 value comprises increasing the current if the updated predicted CEM43 value is below a predetermined value.

19. The system of claim 15, wherein adjusting the current being applied to the rechargeable energy storage device based on the updated predicted CEM43 value comprises decreasing the current if the updated predicted CEM43 value is above a predetermined value.

20. The system of claim 15, wherein adjusting the current being applied to the rechargeable energy storage device comprises adjusting a duty cycle.

21. The system of claim 15, further comprising a memory in communication with the controller; and wherein
the memory includes a lookup table; and
the predicting the cumulative thermal dose associated with charging the rechargeable energy storage device to the fully charged state is based on the lookup table stored in the memory.

22. The system of claim 1, further comprising a charger comprising a second wireless charging interface configured to interface with the first wireless charging interface of the implantable battery and/or communication module and wirelessly provide current to the first wireless charging interface of the implantable battery and/or communication module.

23. The system of claim 22, wherein the first wireless charging interface comprises a first coil and the second wireless charging interface comprises a second coil, and wherein providing current to the second wireless charging interface comprises inductively inducing a current in the second coil.

24. The system of claim 1, further comprising a sense resistor in electrical communication with the first wireless charging interface and the rechargeable energy storage device, and wherein
the controller is configured to receive information indicative of a voltage across the sense resistor; and
the determining the amount of current being provided to the rechargeable energy storage device is based on the voltage across the sense resistor.

25. A method for wirelessly charging a rechargeable energy storage device within an implanted system comprising:
(a) wirelessly applying a current to a rechargeable energy storage device;
(b) determining an amount of current being provided to the rechargeable energy storage device;
(c) measuring a temperature associated with the rechargeable energy storage device;
(d) predicting an amount of time remaining until the rechargeable energy storage device is fully charged;
(e) predicting a cumulative thermal dose associated with charging the rechargeable energy storage device until it is fully charged based on the determined amount of current being provided to the rechargeable energy storage device, the measured temperature, and the predicted amount of time remaining until the rechargeable energy storage device is fully charged;
(f) adjusting the amount of current applied to the rechargeable energy storage device based on the predicted cumulative thermal dose by:
(i) increasing the amount of current applied to the rechargeable energy storage device if the predicted cumulative thermal dose is below a first target value;
(ii) decreasing the amount of current applied to the rechargeable energy storage device if the predicted cumulative thermal dose is above a second target value; and
(iii) maintaining the amount of current applied to the rechargeable energy storage device if the predicted cumulative thermal dose is equal to the first target value, equal to the second target value, or between the first target value and the second target value; and
(g) repeating steps (a)-(f) until the rechargeable energy storage device is fully charged or current is no longer applied to the rechargeable energy storage device.

26. The method of claim 25, wherein the first target value is less than the second target value.

* * * * *